US006383775B1

(12) United States Patent
Duff et al.

(10) Patent No.: US 6,383,775 B1
(45) Date of Patent: May 7, 2002

(54) DESIGNER PROTEASES

(75) Inventors: Gordon W. Duff, Sheffield; Jon R. Sayers, Clay Cross; Srdjan Vitovski, Sheffield, all of (GB)

(73) Assignee: Interleukin Genetics, Inc., Waltham, MA (US)

( * ) Notice: Subject to any disclaimer, the term of this patent is extended or adjusted under 35 U.S.C. 154(b) by 0 days.

(21) Appl. No.: 09/266,498

(22) Filed: Mar. 11, 1999

Related U.S. Application Data

(63) Continuation-in-part of application No. PCT/GB97/02456, filed on Sep. 10, 1997.

(30) Foreign Application Priority Data

Sep. 11, 1996 (GB) .............................. 9618960

(51) Int. Cl.$^7$ ........................... C12P 21/06; C12P 21/04

(52) U.S. Cl. ..................... 435/69.1; 435/7.1; 435/69.7; 435/69.8; 435/70.1

(58) Field of Search ................................ 435/7.1, 69.7, 435/69.8, 70.1, 69.1; 530/350, 370, 371, 380, 381

(56) References Cited

U.S. PATENT DOCUMENTS

| | | | |
|---|---|---|---|
| 5,252,478 A | 10/1993 | Ros et al. | 435/222 |
| 5,268,270 A | * 12/1993 | Meyer et al. | 435/69.1 |
| 5,387,518 A | 2/1995 | Sawayanagi et al. | 435/221 |
| 5,391,490 A | 2/1995 | Varshavsky et al. | 435/224 |
| 5,427,927 A | 6/1995 | Meyer et al. | 435/69.7 |
| 5,602,021 A | * 2/1997 | Dvais et al. | 435/219 |
| 5,605,793 A | 2/1997 | Stemmer | 435/6 |

FOREIGN PATENT DOCUMENTS

| | | |
|---|---|---|
| WO | 2058872 | 1/1992 |
| WO | WO 96 21009 | 12/1995 |

OTHER PUBLICATIONS

J. Koomey et al. "Genetic and biochemical analysis of gonococcal lgA1 protease: Cloning in *Escherichia coli* and construction of mutants of gonococci that fail to produce the activity", PNAS (1982) 79:7881–7885.
M. Zoller et al. "Oligonucleotide–directed mutagenesis using M13–derived vectors: an efficient and general procedure for the production of point mutations in any fragment of DNA", Nuc. Acid. Res. (1982) 10(20):6487–6500.
E. Gilboa et al. "Transfer and Expression of Cloned Genes Using Retroviral Vectors", Bio. Techniques (1986) 4(6):504–512.
T. Meyer et al. "Mechanism of extracellular secretion of an IgA protease by gram–negative host cells", Adv. Exp. Biol. (1987) 216B: 1271–1281.
J. Pohlner et al. "*Neisseria gonorrhoeae* lgA protease. Secretion and implications for pathogenesis", Antoine van Leeuwenhoek (1987) 53:479–484.

J. Gilbert et al. "Cloning of the Gene Encoding Streptococcal Immunoglobulin A protease and Its Expression in *Escherichia coli*", Infect. & Immun. (1988) 56(8):1961–1966.
T. Klauser et al. "Extracellular transport of cholera toxin B subunit using Neisseria lgA protease β–domain: conformation–dependent outer membrane translocation", EMBO J. (1990) 9(6):1991–1999.
A. Tomasselli et al. "Substrate Analogue Inhibition and Active Site Titration of Purified Recombinant HIV–1 Protease", Biochem. (1990) 29:264–269.
Miller et al. "Endoglucanase A from *Cellulomonas fimi* in which the hinge sequence of human lgA1 is substituted for the linker connecting its two domains is hydrolyzed by lgA proteases from *Neisseria gonorrhoeae*" FEMS Microbiol. Lett. (1993) 71(2):199–203.
J. Pohlner et al. "Sequence–Specific Cleavage of Protein Fusions Using a Recombinant Neisseria Type 2 lgA Protease", Bio/Technology (1992) 10(7):799–804.
H. Craig Morton et al. "Purification and Characterization of Chimeric Human lgA1 and lgA2 Expressed in COS and Chinese Hamster Ovary Cells", J. Immunol. (1993) 151(9):4743–4752.
J. Cregg et al. "Recent Advances in the Expression of Foreign Genes in *Pichia pastoris*", Bio/Technology (1993) 11:905–910.
T. Klauser et al. "The Secretion Pathway of lgA Protease–type Proteins in Gram–negative Bacteria", BioEssays (1993) 15(12):799–805.
M. Pompejus et al. "High–yield production of bacteriorhodopsin via expression of a synthetic gene in *Escherichia coli*", Eur. J. Biochem. (1993) 211:27–35.
R. Seizen et al. "Engineering of the substrate–binding region of the subtilisin–like, cell–envelope proteinase of *Lactococcus lactis*", Protein Engineering (1993) 5(8):927–937.
A. Mildner et al. "The HIV–1 Protease as Enzyme and Substrate: Mutagenesis of Autolysis Sites and Generation of a Stable Mutant with Retained Kinetic Properties", Biochemistry (1994) 33:9405–9413.
W. Stemmer "Rapid evolution of a protein in vitro by DNA shuffling", Nature (1994) 370(4):389–391.
P. Walker et al. "Efficient and Rapid Affinity Purification of Proteins Using Recombinant Fusion Proteases", Bio/Technology (1994) 12:601–605.
S. Wong et al. "Engineering and Production of Streptokinase in a *Bacillus subtilis* Expression–Secretion System", Appl. Environ. Microbiol. (1994) 60(2):517–523.
S. Vitovski et al. Invasive Isolates of *Neisseria Meningitidis* Possess Enhanced Immunoglobulin A1 Protease Activity Compared to Colonizing Strains, FASEB J. (1999) 13:331–337.

* cited by examiner

*Primary Examiner*—Jyothsna Venkat
*Assistant Examiner*—Thomas Prasthofer
(74) *Attorney, Agent, or Firm*—Beth E. Arnold; John D. Quisel; Foley, Hoag & Eliot, LLP

(57) ABSTRACT

The invention provides a method for engineering and selecting an active protease able to cleave a user-defined target amino acid sequence. The method is useful for designing proteases for medical therapeutics and industrial applications.

17 Claims, 7 Drawing Sheets pDANGLE

MUTAGENESIS OF PROTEASE DOMAIN

DESIGNER PROTEASES

PRIORITY CLAIM

This application is a continuation-in-part of PCT/GB97/02456, filed Sep. 10, 1997, which claims priority to GB9618960.0, filed Sep. 11, 1996.

FIELD OF THE INVENTION

The present invention relates to means and methods for producing modified self-secreting endoproteases which can cleave user-defined targeted sequences, and such proteases produced by the method.

BACKGROUND OF THE INVENTION

Proteases (peptidases) are proteins which cleave other proteins and have been useful, for example, in the isolation of recombinant proteins. See, for example, U.S. Pat. Nos. 5,387,518, 5,391,490 and 5,427,927, which describe various proteases and their use in the isolation of desired components from fusion proteins.

Self-secreting extracellular proteases, such as IgA proteases, have substrate specificity for IgA (FIG. 1) and are produced by bacteria in the genera Streptococcus, Neisseria, Haemophilus, Ureaplasma, Clostridium, Copnacytophages and Bacteroides (Meyer et al., 1987; Klauser et al., 1993; Pohlner et al., 1987; Morton et al., 1993; U.S. Pat. No. 5,427,927; Canadian patent application 2,058,872). The bacterial IgA proteases are characteristic of the self-secreting endoproteases, in that they are self cleaved and secreted into the extracellular environment. All have substrate specificity for human IgA immunoglobulins, generally for IgA1, which is one of the two IgA isotypes and the dominant IgA form secreted by humans. A self-secreting IgA1 protease attacks a single, specific peptide bond in the heavy chain hinge region of IgA1, resulting in formation of hydrolysis products consisting of the intact antigen-binding Fab and the Fc region of the antibody (FIG. 1).

The synthesis and secretion of IgA1 protease is shown in general in FIG. 2. Though FIG. 2 summarizes a serine type protease, the general mechanism remains similar for other types of proteases. The amino acid sequence required for enzyme activity and secretion in gram-negative bacteria is contained in a single polypeptide chain having 4 domains: 1) a signal peptide sequence; 2) a carboxy-terminal domain; 3) an intervening or α region; and 4) the IgA protease enzyme (Klauser et al, 1993; Koomey et al., 1982; Miller et al., 1992; Pohler et al., 1987).

The signal sequence directs the enzyme precursor to the periplasm, and is proteolytically removed during transport across the cytoplasmic membrane (inner membrane). The remainder of the polypeptide is then determined by the carboxy terminal domain which has eight transmembrane β-sheets, typical of this class of membrane proteins (reviewed in Klauser et al., 1993). The carboxy terminal domain forms a channel through which the amino-proximal end is threaded. The amino-proximal end including the catalytically active part of the protein (protease and α-region) is long and is initially exposed on the outside of the outer membrane before it is cleaved and released.

Autoproteolytic processing at typical cleavage sites (a and b in FIG. 2) in and around the α-region results in the release of the protease from the cell membrane. The a and b sites contain proline-rich sequences similar to the cleavage site of the IgA protease in human IgA1.

The sole secretion factor specifically required for IgA1 protease secretion is an integral part of the protease precursor. There is no need for receptors that specifically select proteins from periplasmic pools for secretion across the outer membrane. In fact, the IgA1 protease secretion pathway may facilitate the outer membrane translocation of virtually any polypeptide that is fused to its amino terminus provided that all other conditions for efficient secretion are met (Pohlner et al., 1993).

The IgA proteases are extensively used as proteolytic enzymes for cleavage of fusion proteins produced by genetic engineering (U.S. Pat. No. 5,427,927). There has been extensive investigation of these proteases and other proteases to improve their activity and to extend their substrate specificity (Canadian patent application 2,058,872; Pohlner et al., 1987; Morton et al., 1993; Gilbert et al., 1988; Koomey et al., 1982; Pohlner et al., 1992; Pohlner et al., 1993; Walker et al., 1994; Pompejus et al., 1993; Wong et al., 1994; Pohlner et al., 1993; Pohler et al., 1992; U.S. Pat. Nos. 5,427,927; 5,252,478; Miller et al., 1992). However, the method of choice for extending the targets of the proteases has been to insert into the target protein the cleavage sequence that is required by the protease. Alternatively, many proteases may be screened until one is found that will cleave at the requisite sequence. Methods of rapidly and efficiently selecting and engineering or designing an existing protease to cleave a new sequence specifically have not been available.

SUMMARY OF THE INVENTION

The present invention provides methods for making and selecting site-specific proteases ("designer proteases") able to cleave a user-defined recognition sequence in a proteins. The invention provides a method for cleaving any protein at an exposed site on the protein. The method includes the steps of incorporating a DNA sequence encoding the target amino acid sequence to be cleaved (recognition sequence) into a tolerant region of a self-secreting protease gene (e.g., the α region or domain of IgA1), thereby replacing the natural cleavage site for autoproteolysis. Expression of this gene leads to accumulation of a surface-bound protease that has the user-defined recognition site incorporated into the portion of the molecule that links the protease to the cell surface. The coding region of the active domain of the protease is then subjected to extensive mutagenesis (e.g., site-directed mutagenesis or Stemmer mutagenesis). Some proteases in the pool of modified proteases will be able to recognize the user-defined recognition sequence and will cleave that site, thereby releasing the active protease from the cell surface. In one embodiment, the self-secreting protease gene used as the starting material for mutagenesis is that encoding a modified IgA1 protease.

In an embodiment of the invention, the designer protease is selected using a negative selection procedure, wherein a cell expressing IgA1 protease on its surface is depleted. For example, affinity chromatography using an antibody specific for the protease (or artificially introduced epitope tag) can be used. In another embodiment, the designer protease is selected using a positive selection procedure, wherein the cleaved protease is detected. In another embodiment, cells producing the designer protease are positively selected. In one embodiment, the DNA sequence encoding the designer protease further encodes an affinity tag which can be used in a positive selection procedure to select bacteria expressing the designer protease. The affinity tag is able to bind to an immobilised ligand which may be, for example, a peptide or a small ligand, such as, for example nickel.

The invention also provides a protease which has been engineered to cleave a user-defined target amino acid sequence encoded by a target DNA sequence, including (a) a signal peptide sequence, (b) a modified protease catalytic domain, (c) an α region comprising a target DNA sequence and (d) a carboxy-terminal domain, wherein the modified protease catalytic domain is able to cleave said target DNA sequence.

In an embodiment, the methods of the invention provide therapeutics for downregulating or inactivating expression of any target protein. The target protein may be overexpressed in humans having a disease such as an inflammatory disease, a genetic disease or a cell regulation disorder. For example, the target protein may be a cytokine or other proinflammatory molecule or acute phase reactant, a cytokine receptor, a blood protein such as a clotting factor, an oncogene, an anti-oncogene or a mutant protein that causes a genetic disorder such as an autosomal dominant disorder. In another embodiment, the target protein may be derived from an exogenous source, for example, from a virus or a bacteria, the method thereby being useful for treating infectious diseases. For example, the target protein may be a viral protein or a bacterial protein especially those that are antibody resistant or that confer antibody resistance, a toxin, an environmental pollutant or an industrial pollutant.

Other features and advantages of the invention will be apparent from the following figures, detailed description, and claims.

DETAILED DESCRIPTION OF THE INVENTION

The present invention provides methods for making (i.e., engineering and selecting) a site-specific, self-secreting protease that is able to cleave a user defined target amino acid sequence (recognition sequence). That is, a self-secreting protease, such as an IgA1 protease, is modified to cleave a target amino acid sequence within the α region of the IgA1 protease that is not its natural target. The self-secreting protease to be modified is selected from proteases that are secreted from a cell and in the process of secretion are attached externally on the cell membrane. To be released from the membrane the protease autocleaves the target amino acid sequence of the molecule thereby being released from the membrane as described more fully herein.

The user defined target amino acid sequence can be from any protein or peptide for which a protease is needed. The amino acid sequence that is the target must be expressed in the protein or peptide molecule in a position that is accessible to the designer protease.

Figure 3A:
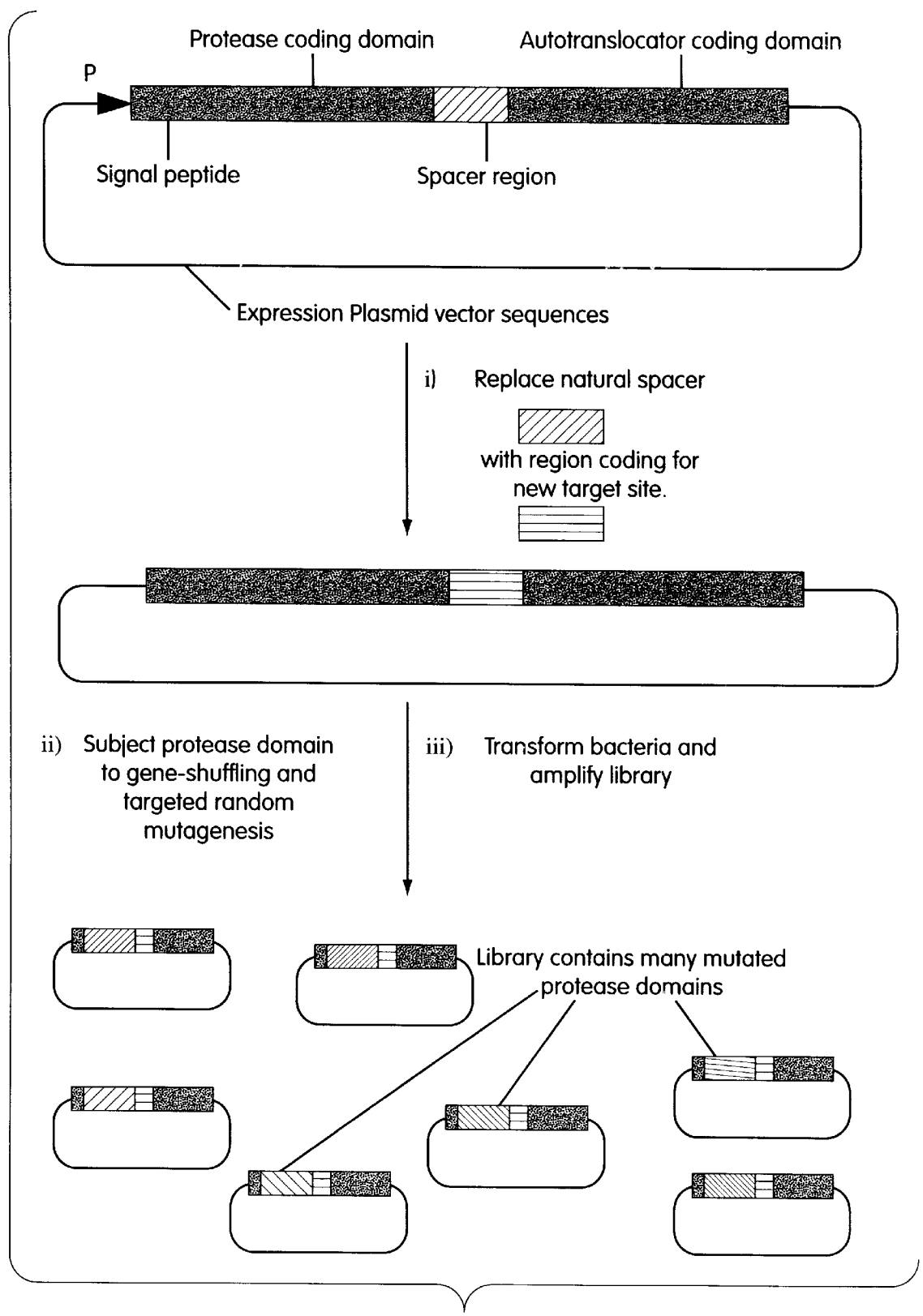
FIGS. 3A and 3B are diagrams of the process of the present invention.
Figure 3B:
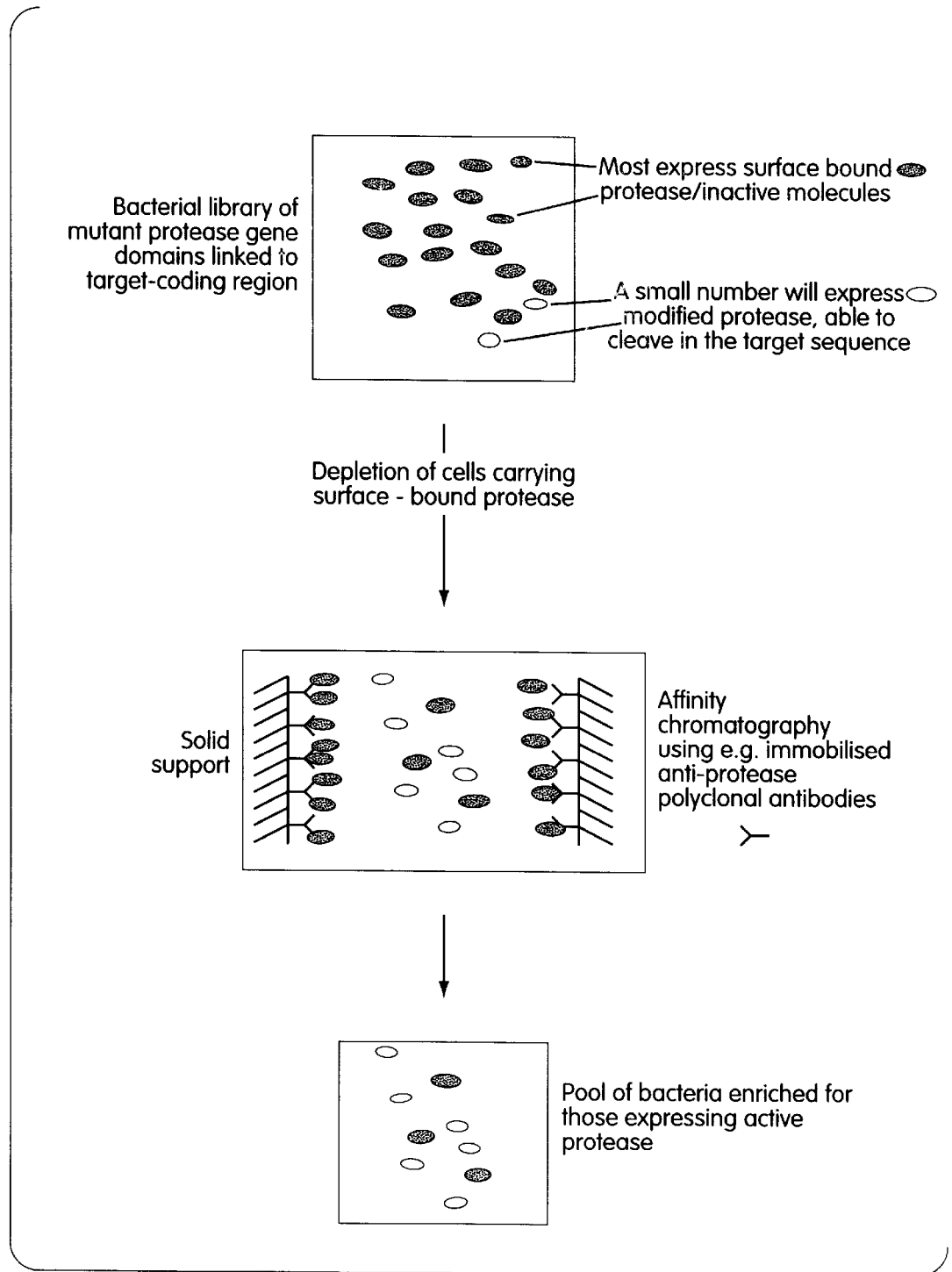
Figure 4:
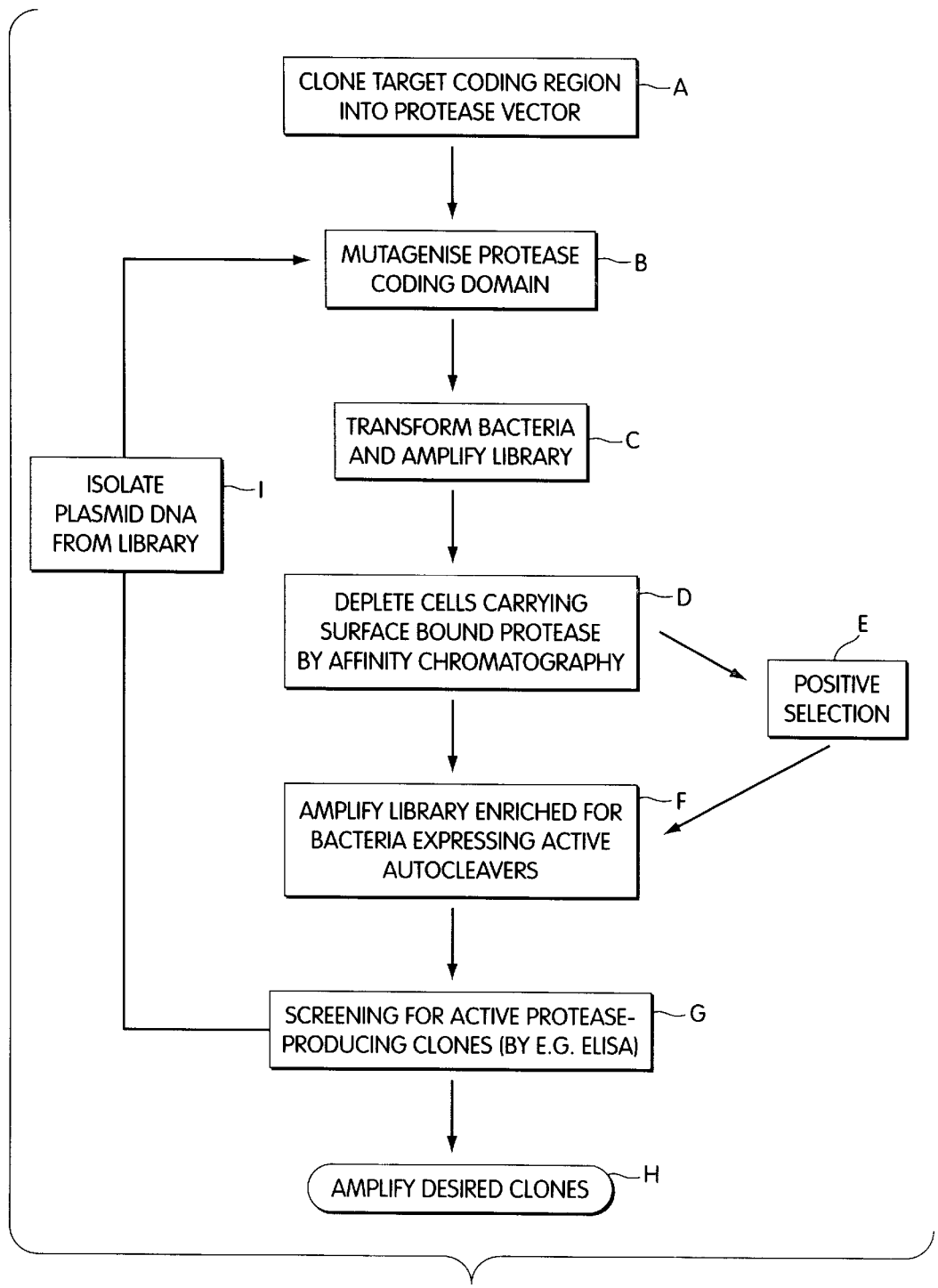
FIG. 4 is a flow diagram outlining the overall processes involved.

The process is shown in FIGS. 3A and 3B. The first step of the process incorporates a DNA sequence for a user defined target amino acid sequence into the gene sequence for the protease between the protease coding domain and the autotranslocator coding domain of the protease DNA sequence. That is, the target DNA sequence is inserted into a tolerant region of a self-secreting protease gene, thereby replacing the natural cleavage site for autoproteolysis for a target cleavage site. Any method known in the art may be used to incorporate the target DNA sequence into the DNA sequence of the self-secreting protease. Standard methods such as site-directed insertion mutagenesis (Sayer et al., 1992) or the introduction of point mutations to alter the coding region while maintaining the reading frame may be used.

The protein sequence of the catalytic domain of the protease containing the incorporated target cleavage site is then modified by subjecting the corresponding protease DNA sequence to in vitro mutagenesis. Any method known in the art can be used to modify the DNA sequence, preferably methods which can be directed to alter a specific region, i.e. the substrate recognition domain, are used (Eglinton et al.; Zoller and Smith, 1982; Wong et al., 1994; Pompejus et al., 1993; Mildner et al., 1994) such as for example, site direct mutagenesis and/or gene shuffling (Stemmer, 1994). A protease encoded by a modified catalytic domain DNA sequence that is able to autocleave the target amino acid sequence is then selected and isolated. Because of the nature of the protease employed, only those proteases carrying the desired cleavage mutation will be soluble, i.e., will be released from the cell membrane.

Definitions

The meaning of certain terms and phrases as used in the following detailed description and claims are defined as follows:

The terms "mutagenized catalytic domain" and "modified catalytic domain" are used interchangeably herein and refer to the proteolytic region of the designer protease which has been mutated or modified to recognize a cleavage site, e.g., which has been replaced or altered (the "mutagenized cleavage site").

The terms "mutagenized cleavage site", "mutagenized target site", "modified cleavage site", "modified target site", "user-defined cleavage site" and "user-defined target site" are used interchangeably herein and refer to a cleavage site which has been altered and replaced from the naturally occurring self-secreting protease. The mutagenized cleavage site may be a protein sequence derived from a protein of interest. The mutagenized cleavage site is preferably a sequence that is externally exposed or which is accessible to a protease in vivo.

The term "protease catalytic domain" refers to the catalytic and substrate binding region of the self-secreting protease which is capable of cleaving a natural cleavage site of the self-cleaving protease.

The terms "self-secreting protease" and "self-cleaving protease" are used interchangeably herein and refer to the full length protease, which contains at least 1) a signal peptide sequence; 2) a carboxy-terminal domain; 3) an intervening or α region (natural target site); and 4) the protease enzyme (catalytic region).

The term "therapeutic" refers to various forms of polypeptides, as well as peptidomimetics, nucleic acids, or small molecules, which can modulate at least one activity by, e.g., regulating the expression of a gene, by mimicking, potentiating (agonizing) or inhibiting (antagonizing) the effects of a naturally-occurring cell or polypeptide.

Choice of Self-Cleaving Protease

The invention provides methods for designing and making a protease which cleaves a specific user-defined target site derived from a protein, for example, a protein which requires downregulation or inactivation. An IgA1 or any other self-secreting protease may be used as the starting material to design a protease which can cleave an amino acid sequence of interest. IgA proteases (IgAses) are naturally exported by some Gram negative bacteria (Meyer et al., 1987). These bacteria include but are not limited to *Streptococcus sanguis, Streptococcus oralis* (Gilbert et al., 1988; Morton et al., 1993), *Neisseria gonorrhoeae, Neisseria meningitidis, Haemophilus influenzae* (Klauser et al, 1993; Koomey et al., 1982; Miller et al., 1992; Pohler et al., 1987).

The IgA proteases are a group of homologous proteins each with its own unique cleavage specificity directed at specific sites on an IgA molecule. As discussed herein above, the protein is synthesized as a fusion of protease, α peptide and autotranslocator domains (Klauser et al, 1993; Meyer et al., 1987; Pohler et al., 1987). Given that natural variants of the IgA proteases have different sequence specificities, the above system will be capable of generating huge numbers of mutant proteases some of which will have novel sequence specificities. The natural IgAses have low immunogenicity and so designer proteases will be best utilized to target important mediators of inflammatory processes, hormones, viral proteins, microbial proteins, proteins that regulate cell cycle, oncogene products and enzymes, etc.

Figure 1A:
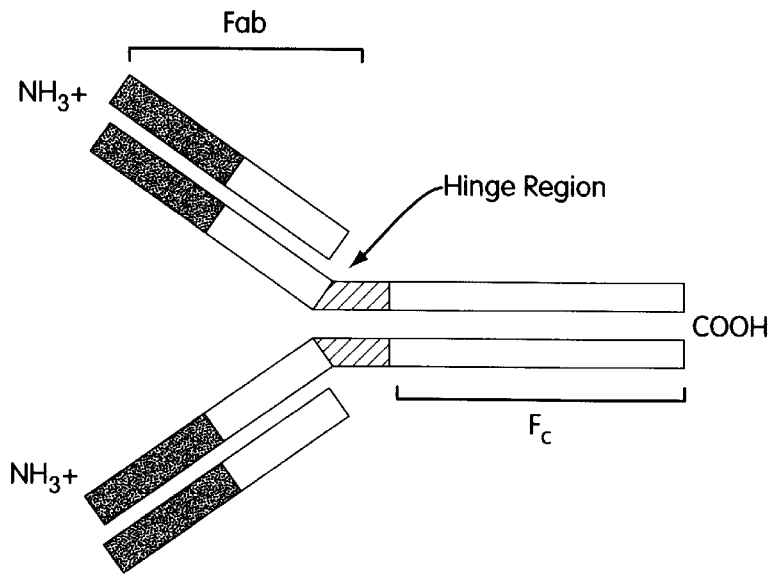
FIGS. 1A and 1B are diagrams wherein (A) is a diagram of an IgA molecule showing the variable region (shaded), constant regions (nonshaded) and hinge (shaded) and (B) is a diagram of the primary sequence of the IgA1 hinge region showing peptide bonds cleaved by various listed IgA1 proteases.
Figure 1B:
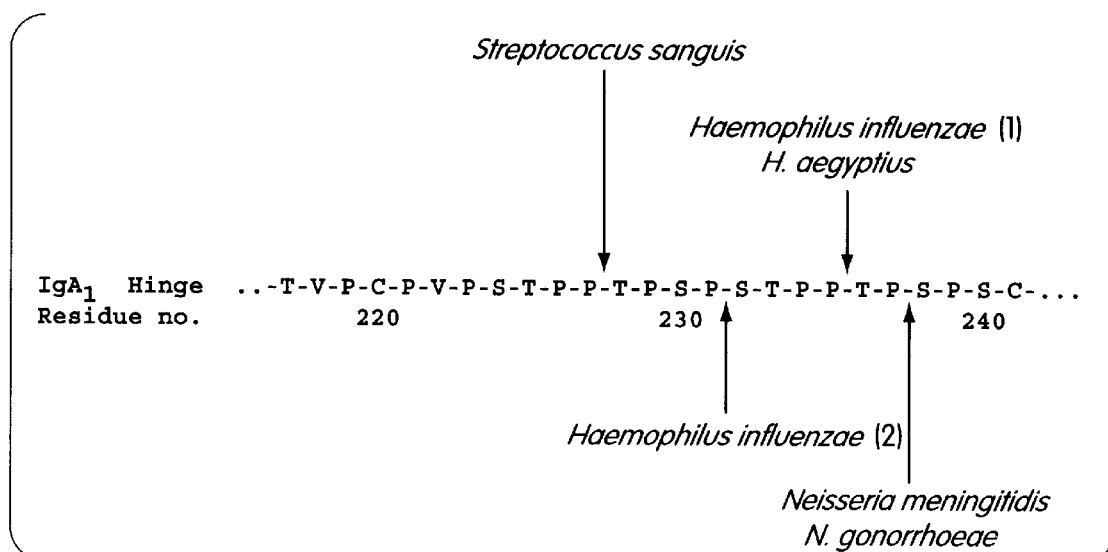
Figure 2:
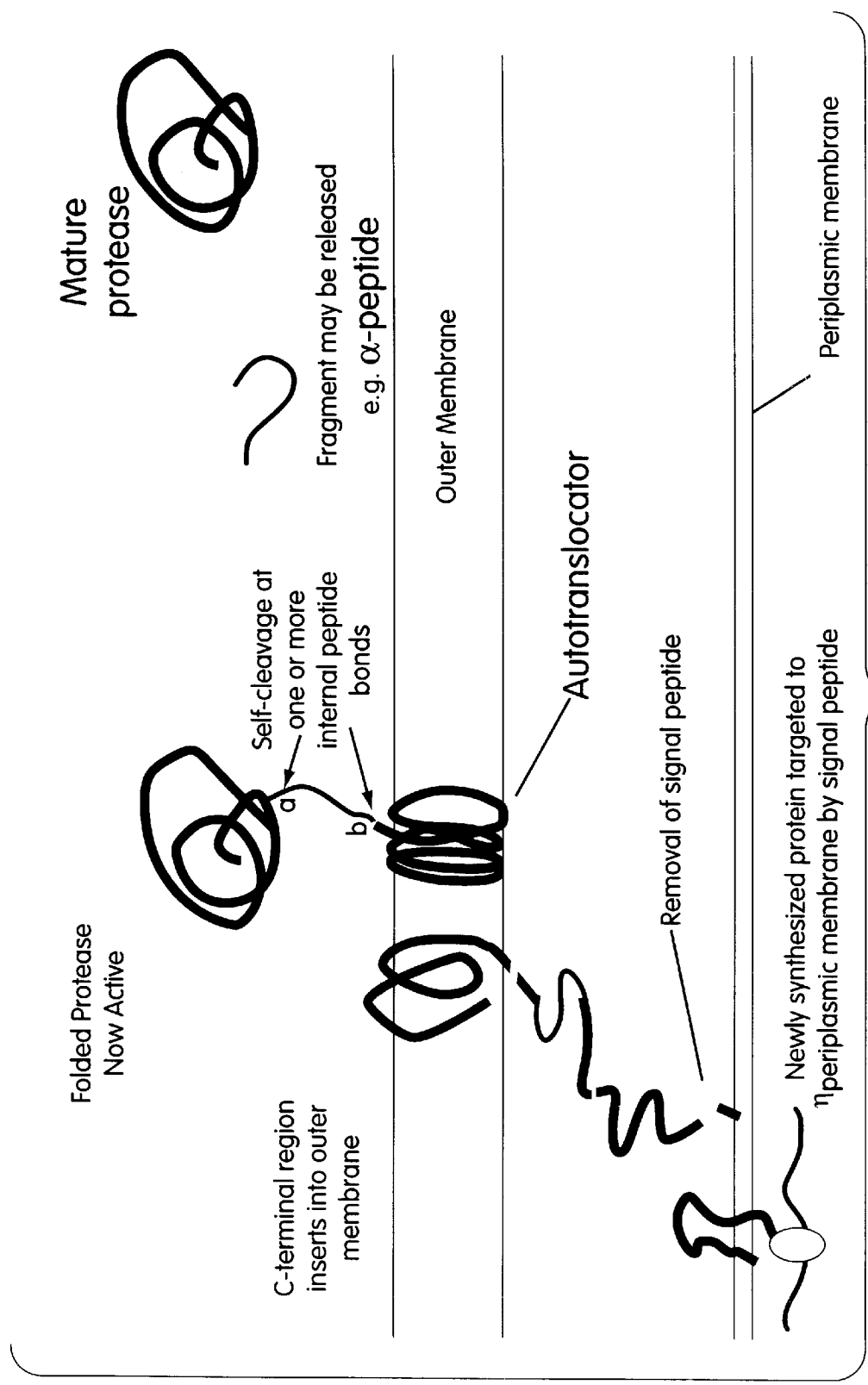
FIG. 2 is a diagram of a model for the extracellular secretion of an IgA1 protease.

As shown in FIG. 2, the preprotein is transported to the cell surface where it folds and undergoes autocleavage at internal recognition sites to produce free mature protease. Once translocated to the outside of the cell, the protease domain folds into it's active conformation. It then cleaves itself from the autotranslocator by cutting its specific recognition sequence present in the α peptide region. Mutants which lack the protease's recognition site are known to remain tethered to the outer membrane.

Choice of Target Protein

The self-cleaving protease is also modified to contain a desired target cleavage site and further modified to mutate the protease into recognizing and cleaving the new target site. The desired target cleavage site may be a region of any target protein which is undesirable. Target proteins that participate in the pathogenesis of disease or participate in an industrial or environmental processes, e.g., as a byproduct as useful targets.

a. Clinical Applications

In a preferred embodiment of the invention, a protease is designed to cleave a toxic or pathologic protein which is associated with, or the cause of, a disease in an animal (e.g., a human), thereby promoting clearance of the protein (e.g., for example, by ubiquitin-dependent pathways). A number of diseases are caused or exaccerbated by the overproduction or inappropriate production of a protein. Such diseases can be grouped roughly into four categories: infectious diseases, inflammatory diseases, cell regulation disorders and genetic defects.

In a preferred embodiment, the invention can be used to design and make a protease that will treat or prevent a life threatening or debilitating infectious disease such as, for example, AIDS and Hepatitis C. In addition, any viral, bacterial or fungal protein required for its growth and/ or replication can be targeted with a designer protease. For example, the HIV-1 protease is perceived as a target for development of drugs against AIDS (Mildner et al., 1994; Tomasselli et al., 1990). In addition, two other enzymes crucial to HIV-1 infectivity and replication include reverse transcriptase and integrase. In a preferred embodiment, designer proteases could be made targeting each one specifically and used either alone or in combination as an HIV therapeutic. Alternatively, the proteins gp120 and/or gp41, which together form the gp160 complex, which is required for attachment of HIV to CD4+ cells, would provide effective target proteins for the designer protease. In another embodiment combination therapies of designer proteases with current treatment regimes may be used to help avoid selection of resistant strains of HIV.

In another preferred embodiment, the invention can be used to design and make a protease that will treat or prevent a life threatening or debilitating inflammatory disease such as, for example, rheumatoid arthritis or emphesema. Proinflammatory cytokines such as interleukin 1 (IL-1), interleukin 6 (IL-6) and tumor necrosis factor alpha (TNF-α) could be downregulated or inactivated by specific designer proteases in order to down regulate a chronic inflammatory response. Complement components, proteases or other acute phase reactants that cause collateral damage when chronically produced may also be downregulated. In addition, elevated levels of plasminogen activators urokinase-type (uPA) and tissue-type (tPA) plasminogen activators have been documented in inflammatory infiltrates and would therefore be useful targets for the designer protease. These designer proteases would be particularly useful to individuals with faulty or insufficient plasminogen activator inhibitor (PAI-1) function. The designer protease would provide therapeutics for diseases that are caused by an imbalance between proteases and their inhibitors, such as lung emphysema, caused by alpha1 anti-antitrypsin deficiency, cystic fibrosis and AIDS (e.g., by targeting neutrophil elastase). In another embodiment, the designer proteases of the invention may target pathogenic factors produced by bacteria. For example, a useful target protein would be argingipain, an extracellular cysteine protease produced by the anaerobic rod *Porphyromonas gingivalis*, which is a major pathogenic factor of progressive inflammatory periodontal disease (Kadowaki, T. et al., 1994).

In yet another preferred embodiment, the invention can be used to design and make a protease that will treat or prevent a life threatening or debilitating genetic disease such as an autosomal dominant or autosomal recessive disorder. In particular, the instant invention is useful for treating a disease which is caused by a nonfunctional or insufficiently expressed protease. For example, a designer protease directed at von Willebrand factor would be useful as a therapeutic for treating chronic relapsing thrombotic thrombocytopenic purpura, a disease caused by deficient activity of von Willebrand factor-cleaving protease (Furlan, M. et al., 1997).

In still another preferred embodiment, the invention can be used to design and make a protease that will treat or prevent a life threatening or debilitating disease stemming from faulty cell cycle or cell growth regulation, such as cancer. For example, a designer protease targeting Her-2/neu oncogene would be effective in treating some ovarian and breast cancers.

b. Medical Devices

The proteases produced by the instant invention may be administered to a patient as a pharmaceutical preparation as described herein below and according to any of a number of other art known methods, or may be used in conjunction with a medical devise, such as, for example, a catheter or a dialysis machine. For example, blood may be cleared of a pathologic protein by passage of blood through a dialysis unit containing the designer protease. The designer protease may be bound to the surface of beads contained within the cartridge or column over which the blood is passed and the target protein cleaved by the protease. Such devices and methods are well known in the art and may be useful in the rapid clearance of a bloodborne proteinaceous pathogens.

c. Industrial Applications

The instant invention has wide applications to essentially any industrial process which requires the cleavage of a protein or removal of a protein byproduct, in particular those proteins for which there is no known protease, those requiring a specific protease or those proteins for which cleavage at a particular site is desired.

In one embodiment, the invention provides a method for designing and making a protease which can be useful in the manufacture of any protein that is produced using fusion protein methods, where the target protein needs to be recovered intact (e.g., recombinant insulin tagged to GST can be cleaved off neatly by the protease thrombin). Sequence specific endoproteases such as wild-type IgA1 protease, thrombin and factor Xa have been used in the processing of fusion proteins for protein engineering work and in biotransformations, however, the number of sequence specific proteases is very limited at present and often produce fusions with undesired additional amino acid residues. In this context a designer protease could be engineered for accurate cleavage or processing of a particular fusion or preprotein. The instant invention will allow such a protein to be cleaved specifically at any sterically permissible target site or will allow for the use of any desired tag sequence, the DNA sequence of which can be used to design a protease to cleave the tag specifically.

In another embodiment, the invention can be used to design and make a protease that will have industrial applications, such as in the food, beverage, cosmetic, textile, and leather industries. The most common use may be in the leather industry, where protease preparations are used in different steps of leather processing. Another usage is in the preparation of detergents, for example, laundry detergents, in which proteases are added to cleave plant and blood proteins. Proteases are used in brewing, baking, and in a variety of food products (e.g., soy sauce processing, manufacture of protein-based flavor bases, etc.). The proteases employed in these industries are usually derived from bacteria or fungi. The preparations are often crude and the exact composition and nature of the proteases are not precisely known. For example, a variety of preparations from different manufacturers can be used in the dehairing of leather. Application of a designer protease(s) can be used, particularly if the structure of the protein target is known. For example, removing "haze" or "chill haze" from beer may be achieved by a designer protease of the instant invention, since the structure of some of the proteins which constitute haze are known. Since there are several proteins in the haze, it will require several designer protease(s), which may again be unique for a brand of beer or for a specific brewer.

d. Environmental or Occupational Health Applications

In another embodiment, the invention can be used to design and make a protease that will have environmental applications, such as decontaminating or neutralizing protein toxins such as botulinum or spore-free anthrax, cholera toxins, diptheria toxins or neurotoxins, peptide hormones, undesirable proteins in effluent from fish farms or other intensive animal husbandry sites.

Choice of Target Site

Once a target protein is chosen, a desired target cleavage site is determined, for example by biological assay, crytallographic data or computer modeling of the protein. FIG. 3 provides a diagram of the construction of designer proteases of the present invention. For example, in an embodiment, certain proteases are known to be critical to cancer cell growth and it is therapeutically useful to have anti-proteases available. The target protein is analyzed chemically and structurally to determine if there are unique amino acid sequences that can be used as a target of the designer protease of the present invention. The DNA coding for this unique sequence is then determined and is used to replace the sequence in the $\alpha$ region (e.g., at ab in FIG. 3) of the IgA1 protease gene. The desired target DNA cleavage site is then inserted into, or used to replace, the natural protease cleavage site of the natural self-secreting protease. Any number of methods can be employed by the skilled artisan to introduce the target cleavage site into the DNA coding sequence of the protease DNA sequence as described herein below, such as, for example site directed mutagenesis. The modified self-cleaving protease is then selected for using standard molecular biological screening techniques well known in the art and described herein below.

Mutagenesis of the Catalytic Region of the Protease

The preparation of a designer protease requires mutagenesis of the catalytic region of the protease to create a library of mutagenized preoteases from which ones that acquire the ability to cleave the new target site can be selected and isolated. This may be accomplished, for example, using one or more rounds of site directed mutagenesis or gene shuffling. For example, the protease gene sequence is first amplified by PCR and the PCR products are randomly cut into fragments by DNAaseI. Gel purification of small fragments and reassembly of the fragments in a PCR-like reaction without primers is then undertaken. Amplification of the reassembled product can be undertaken by PCR followed by cloning into a vector such as a plasmid. Up to $10^9$ mutant clones can be generated from each round of gene shuffling. This library of modified clones can then be transferred to a host cell, which will express the mutant protein from the mutated gene sequence. As shown in FIG. 3(ii), a combination of the Stemmer mutagenesis (1994) and more classical site-directed protocols can be used. This procedure generates large numbers of combinatorially mutated plasmids (up to $10^9$ different clones per library). The library is then expressed in an appropriate host cell, many of which are well known in the art, for example *E. coli*.

Selection of the Designer Protease

The library is then subjected to a selection process to identify and isolate the mutant proteases that are capable of self-cleavage. The selection process is based on the fact that transformants containing mutant proteases that fail to cleave (hydrolyze) the desired target cleavage sequence in the α region of the protease will retain protease bound on the cell membrane and can be depleted using standard methods known in the art, i.e. negative selection or positive selection. Cells which carry active mutant protease genes capable of cleaving somewhere in the user defined target sequence expressing soluble, rather than surface-bound protease. For example, for negative selection, antibodies specific for an unmodified region of the protease can be mixed with the cells and complement mediated lysis can be used. Alternatively, the specific antibodies can be immobilized on a solid support such as an affinity column and used to selectively remove the cells with surface bound protease. Cells are washed to remove soluble protease and then subjected to negative selection using immobilized polyclonal or monoclonal antibodies. These can be directed against a recombinant sequence tag expressed on the protease N-terminal or polyclonal anti-protease antibodies could be used (as mutant proteases are still likely to be recognized by a proportion of polyclonals). Thus, cell suspensions are depleted of bacteria carrying surface bound protease. Cell sorting (e.g., fluorescence activated cell sorting (FACS)) could also be used to remove cells that are "tagged" with labeled antibodies.

Alternatively, positive selection can be used to identify and isolate the designer proteases of the invention. That is, enrichment can be based on selecting cells which do not have proteases bound to the cell membrane surface. For example, the cell media for a single clone or pool of clones can be assayed for the presence of soluble protease in the media, using an immunoassay. Alternatively, a functional assay for the presence of the protease could be undertaken.

In a preferred embodiment, a combination of negative and positive selection is used. For example, negatively selected cells, enriched for cells lacking surface bound protease, are amplified/cloned and then subjected to a positive screening step. This involves screening individual clones for production of soluble protease. This can done either using polyclonal antibodies directed to the protease (to detect clones which do produce soluble protein) in an immunoassay or by using a functional assay which utilizes a peptide containing the target sequence. Such screening procedures are carried out on many thousands of clones selected from the primary negative screen.

This procedure leads to the isolation of proteases able to cleave somewhere within the desired target sequence and the procedure produces at least one, but generally several, clones with a number of different cleavage specificities for any given polypeptide target sequence. The process can be made iterative at either stage leading to the isolation of more proteases with improved catalytic activities/specificities.

The above procedure can also be modified to use other proteases, e.g., of human origin, by replacing the IgAse domain with the protease of interest. A system based on the above outline can also select for chemical synthesis of proteins from peptide (or even non-peptide) precursors which could have uses in the synthesis of biologically active molecules.

In general, this approach allows negative manipulation of proteins through cleavage at sites necessary for defined biological activity and also positive biological regulation by, for example, increasing rates of processing of bio-active materials from endogenous precursor molecules that is an improvement over the methods of the prior art (Walker et al., 1994; Pompejus et al., 1993; Wong et al., 1994; Pohlner et al., 1993; Pohler et al., 1992; U.S. Pat. No. 5,427,927).

Pharmaceutical Preparations

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, eye drops, injection, inhalation or insufflation (either through the mouth or the nose) or oral, buccal, parenteral or rectal administration.

The carrier can be a solvent or dispersing medium containing, for example, water, ethanol, polyol (for example, glycerol, propylene glycol, liquid polyethylene glycol, and the like), suitable mixtures thereof, and vegetable oils. Examples of delivery systems useful in the present invention include: U.S. Pat. Nos. 5,225,182; 5,169,383; 5,167,616; 4,959,217; 4,487,603; 4,486,194; 4,447,233; 4,447,224; 4,439,196; and 4,475,196. Many other such implants, delivery systems, and modules are well known to those skilled in the art.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the protease and delivery system.

For such therapy, the compounds of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. The formulation and administration of the designer proteases of the invention preferably maximize the activity and stability of the protease.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The designer protease may be administered alone or in combination with other molecules known to also cleave the target protein or to enhance the half-life of the protease. Other useful cofactors include symptom-alleviating cofactors, including antiseptics, antibiotics, antiviral and antifungal agents and analgesics and anesthetics.

A designer protease also may be associated with means for targeting the designer protease to a desired tissue. Alternatively, an antibody or other binding protein that interacts specifically with a surface molecule on the desired target tissue cells also may be used. Such targeting molecules further may be covalently associated todesigner protease, e.g., by chemical crosslinking, or by using standard genetic engineering means to create, for example, an acid labile bond such as an Asp-Pro linkage. Useful targeting molecules may be designed, for example, using the simple chain binding site technology disclosed, for example, in U.S. Pat. No. 5,091,513.

Preparations for oral administration may be suitably formulated to give controlled release of the active compound. For buccal administration, the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the body, e.g., the eye, or other organs without causing inflammation or ischemia. The administered therapeutic is slowly released from these microspheres and taken up by surrounding tissue cells (e.g., endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for a therapeutic designer protease can be introduced into a patient by any of a number of methods, each of which is familiar in the art. For instance, a pharmaceutical preparation of the gene delivery system can be introduced systemically, e.g., by intravenous injection, and specific transduction of the protease in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), *Proc. Natl. Acad. Sci., USA* 91: 3054–3057. A designer protease or a sequence homologous thereto can be delivered in a gene therapy construct by electroporation using techniques described, Dev et al. (1994), *Cancer Treat. Rev.* 20:105–115.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Effective Doe

The designer protease produced by the present invention when used as a therapeutic or medicament is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

Toxicity and therapeutic efficacy of such compounds can be determined by standard pharmaceutical procedures in cell cultures or experimental animals, e.g., for determining the $Ld_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_5/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The doses may be single doses or multiple doses over a period of several days. The treatment generally has a length proportional to the length of the disease process and drug effectiveness and the patient species being treated.

The above discussion provides a factual basis for the method of producing designer proteases as well as for the designer proteases themselves. The methods used with and the utility of the present invention can be shown by the following.

Standard Methods

Standard methods in immunology known in the art and not specifically described were generally followed as in Stites et al.(eds), *Basic and Clinical Immunology* (8th Edition), Appleton & Lange, Norwalk, Conn. (1994) and Mishell and Shiigi (eds), *Selected Methods in Cellular Immunology*, W.H. Freeman and Co., New York (1980).

If needed, ELISAs and RIAs are in general the immunoassays employed. ELISA assays are well known to those skilled in the art. Both polyclonal and monoclonal antibodies can be used in the assays. Where appropriate other immunoassays, can be used as are known to those in the art. Available immunoassays are described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al., *Molecular Cloning: A Laboratory Manual*, Cold Springs Harbor, New York, 1989

Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Maryland (1989). Polymerase chain reaction (PCR) was carried out generally as in *PCR Protocols: A Guide To Methods And Applications*, Academic Press, San Diego, Calif. (1990).)

Reactions and manipulations involving nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference.

Gene Shuffling can be done according to Stemper, 1994. Site Directed Mutagenesis can be done according to Sayer et al, 1992. Vectors can be constructed containing the cDNA of the present invention by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells by any one of a variety of known methods within the art. The host cell can be any eucaryotic and procaryotic cells, which can be transformed with the vector and which will support the production of the enzyme. *E. coli* and *Pichia pastoris* are preferred host cells in bacterial and yeast (Cregg et al, 1993), respectively. Methods for transformation can be found in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa, et al. (1986) and include, for example, stable or transient transfection, lipofection, electroporation and infection with recombinant viral vectors. In addition, see U.S. Pat. Nos. 5,464,764 and 5,487,992 for positive-negative selection methods.

Antibodies used for selection may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W.H. Freeman and Co., 1992.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies the technique involves hyperimmunization of an appropriate donor with the protein or peptide fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or toxin or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination. The toxins can include plant toxins such as ricin, bacterial toxins such as diptheria toxin.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., Sambrook, Fritsch and Maniatis (eds.) (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins, eds., 1984); *Transcription And Translation* (B. D. Hames & S. J. Higgins, eds., 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos, eds., 1987, Cold Spring Harbor Laboratory); *Methods In Enzymology*, Vols. 154 and 155 (Wu et al., eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986); Rossner, B., *Fundamentals of Biostatistics*, Duxbury Press, Belmont, Calif., 370–377, 199; Lewin, B., ed. *Genes VI*, Oxford University Press, UK, 1998.

Throughout this application, various publications, including United States patents, are referenced by citation or number. Full citations for the cited publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims, the invention may be practiced otherwise than as specifically described.

Exemplification

Construction of a Typical "Dangling" Mutant Strain for Use in Production of a Designer Protease

EXAMPLE 1

Cloning of Functional Protease

*Neisseria meningitidis*, strain NMB DNA was used as template in a PCR reaction designed to amplify sections of the IgA1 protease gene using standard conditions. Primers based on the known iga sequence (accession number X82474) were used as follows:

Primer #1 5'-ACCCTTAAAACGGTAAAACCTTATG-3' (SEQ ID NO: 1)

Primer #2 5'-AGAGGATCCGGAGCGGTCTTG TACGGATGA-3' (SEQ ID NO: 2)

These primers amplify the mature protease-encoding region of the iga gene on a fragment of approximately 2.9 kbps. Primer #2 incorporates a BamHI site (underlined). The resultant fragment was gel purified, treated with Klenow fragment to remove the Taq polymerase, non-templated A additions and phenol extracted by standard methods. The fragment was then treated with BamHI.

Primer #3 5'-TCAGGAAGGGCTGAATCTCTTT-3' (SEQ ID NO: 3)

Primer #4 5'-ATGCCGTCTAGAGCCTGAGTTC-3' (SEQ ID NO: 4)

Primers #3 and #4 were used to amplify a region overlapping with the 3' end of the above PCR product (containing a natural NsiI site) and the remaining distal end of the iga (approx. 2 kbps). Primer #4 incorporates an XbaI site (underlined). The resultant fragment was gel purified and treated with NsiI and XbaI.

Plasmid pUC18 was treated with EcoRI and XbaI and used in a triple ligation reaction with the proximal and distal PCR products. This produced a pUC derivative in which the complete IgA1 protease gene was under the control of the lac promoter.

The ligation mixture was then used to transform *E. coli* and a number of recombinants were selected for further study on the basis of restriction digest patterns. One clone (a plasmid designated "pIgA1prot15"), was able to express functional IgA1 protease (after a three hour induction of the Plac using 0.5 mM IPTG in LB media at 37° C.) (see assay in Vitorski, et al., 1999) was selected for further work. The EcoRI-XbaI fragment was also subcloned into pT7T3alpha18 using from pIgA1prot15. This vector is essentially similar to pUC18, allowing expression from the Plac but with the benefit that it carries a phage origin of replication allowing for the production of single-stranded phagemid. This construct is useful for mutagenesis protocols (see below).

EXAMPLE 2

Alteration of Natural Cleavage Sites Within Protease Precursor

Figure 5A:
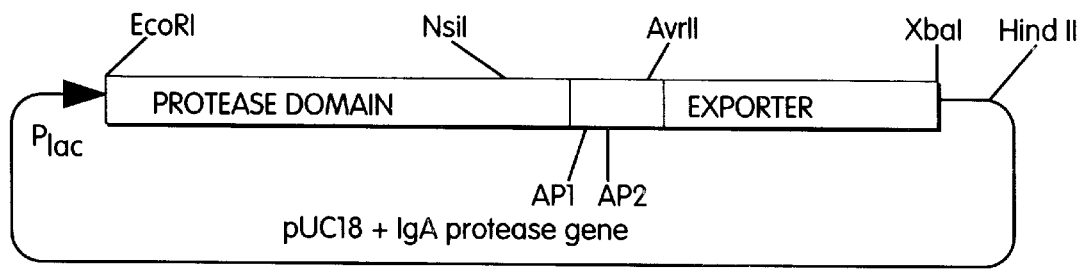
FIGS. 5A–C are diagrams wherein (A) is a Schematic diagram of parental vector producing recombinant IgA1 protease. Restriction sites are as shown. Plac, lac promoter. AP1 and AP2, sites for autoproteolysis in natural protein. Base vector is pUC18; (B) shows that site directed mutagenesis can be used to insert unique restriction sites flanking the natural cleavage sites of the enzyme; and (C) shows the sequence between the BamHI and BglII sites can be exchanged with a cassette (synthetic oligo or suitable PCR fragment) so as to exchange the natural cleavage site for a region encoding the target sequence and (optional) affinity tag.
Figure 5B:
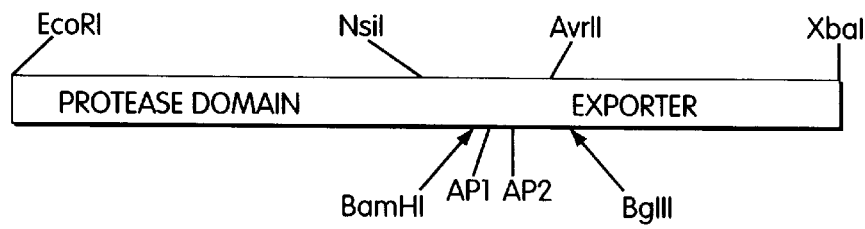
Figure 5C:
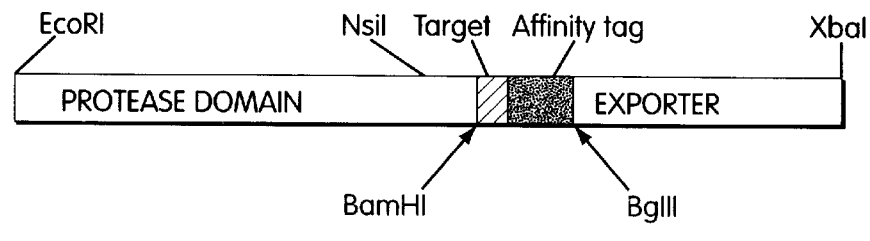

The region of the iga gene encoding the natural target sequence is contained within an NsiI-AvrII fragment (FIG. 5). This region encodes two potential autoproteolytic sites (AP1 and AP2, see below); the cleavage sites are located between the underlined amino acids:

974 Pro Val Pro Ser Pro Ala Thr Asn Thr Ala Ser Gln Ala Gln Thr Asp Ser Ala Gln Ile Ala Lys Pro Gln Asn Ile Val Val Ala Pro Pro Ser Pro Gln Ala Asn Gln Ala 1011 (SEQ ID NO:5)

Several strategies can be employed to abolish these cleavage sites. Using standard PCR-based mutagenesis methods (Ho, et al. (1989) Gene 77:51–59 and chapters in Directed Mutagenesis, A Practical Approach, Ed. M. J. McPherson, Oxford University Press, 1993 ISBN 0-19-963140-9), the coding sequence was altered so as to abolish the two cleavage sites. The mutated site is underlined in SEQ ID NO:6:

974 Pro Val Glu Ser Pro Ala Thr Asn Thr Ala Ser Gln Ala Gln Thr Asp Ser Ala Gln Ile Ala Lys Pro Gln Asn Ile Val Val Ala Pro Glu Ser Pro Gln Ala Asn Gln Ala 1011 (SEQ ID NO:6);

or amino acids 975–1006 were deleted and 6 histidines inserted in SEQ ID NO:7:

974 Pro HIS HIS HIS HIS HIS HIS Gln Ala Asn Gln Ala 1011;

or the entire region can be removed from the construct (FIG. 5C) (deleting amino acids 969–1256) and this region replaced with a target-encoding cassette. Such alterations will result in the expression of surface-bound protease. By introduction of suitable restriction sites flanking the natural autoproteolytic cleavage sites it will be possible to incorporate a DNA fragment (PCR product or synthetic oligonucleotide cassette) encoding the desired protein cleavage sequence with or without a region encoding an affinity tag (see below).

EXAMPLE 3

Evolution of Altered Protease Specificity

A number of mutagenesis strategies could be applied to alter the coding region of the protease domain. Preferentially, the gene encoding the dangling mutant will be subjected to localised mutagenesis procedures using standard techniques such as one or more of the following:

a) The protease-encoding region (in our example, the region between the EcoRI and NsiI sites) has been subjected to various low fidelity PCR-based procedures (Fromant, M. et al. (1995) Analytical Biochemistry, 224:347–353). Unbalanced nucleotide triphosphate pools in which one of the nucleotides is present at 10 times the normal concentration in the presence of $Mn^{2+}$ as cofactor were used during the amplification of the protease-domain encoding fragment. PCR products are then cut with NsiI and EcoRI and re-inserted into the pDANGLE plasmid, transformed into E. coli creating a library of mutant protease genes.

b) The same fragment as above could also be amplified using synthetic nucleoside analogs designed to introduce very high levels of mutations into PCR products (Zaccolo, M. et al. (1996) J. Mol. Biol. 255:589–603). Again the EcoRI/NsiI fragment pool would be re-introduced into the EcoRI/NsiI pDANGLE vector and transformed, creating another library of mutants.

c) Single-stranded DNA prepared from the phagemid version of a pDANGLE plasmid can be used for the highly efficient localised mutagenesis methods. Essentially, any region of the coding sequence desired can be targeted with long (about 50 nucleotides or more) complementary oligonucleotides which have been "spiked" so as to contain a low percentage of each of the three "wrong" nucleotides at each position in the oligo (Chapter 9 in Directed Mutagenesis, A Practical Approach, Ed. M. J. McPherson, Oxford University Press, 1993 ISBN 0-19-963140-9). Published in vitro selection and transformation protocols yield large and highly degenerate libraries.

EXAMPLE 4

Figure 6A:
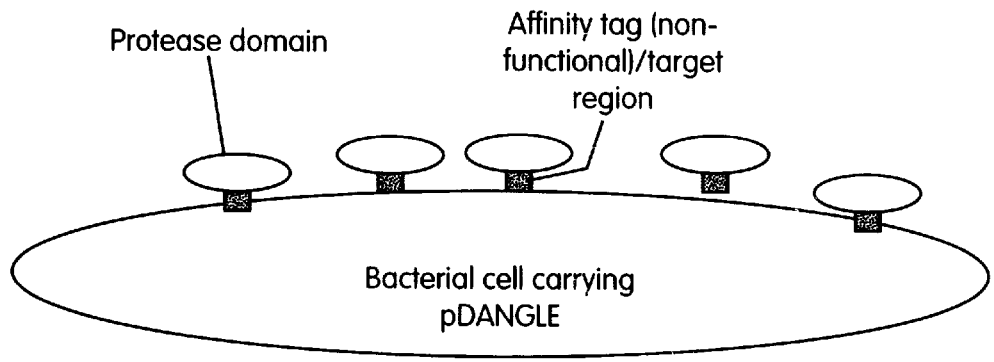
FIGS. 6A–E are diagrams wherein (A) shows clones expressing pDANGLE (upon induction with IPTG) produces surface bound (dangling) IgA1 protease. The affinity tag may be masked by the steric bulk of the large globular protease domain (around 900 residues). Extensive mutagenesis of the protease domain-encoding region will lead to one of 4 different outcomes. (B) shows an altered active site able to cleave within (or near) target sequence, protease "unmasks" the affinity tag rendering it functional and able to bind to immobilised ligand. (C) shows a mutant protease cleaving downstream of, or within, the affinity tag. These cells are unable to bind immobilised matrix. (D) shows that the mutant has no effect on catalysis or expression. These cells again cannot bind matrix. (E) shows that mutations reduce or abolish surface expression of the protease. Only type B cells can bind matrix.
Figure 6B:
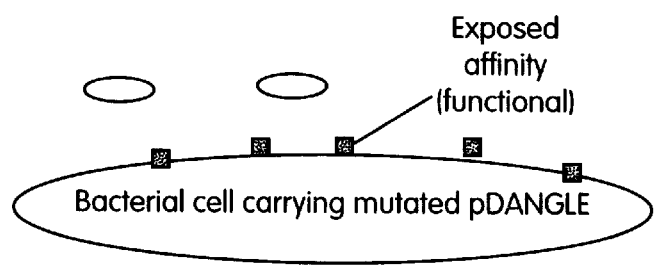
Figure 6C:
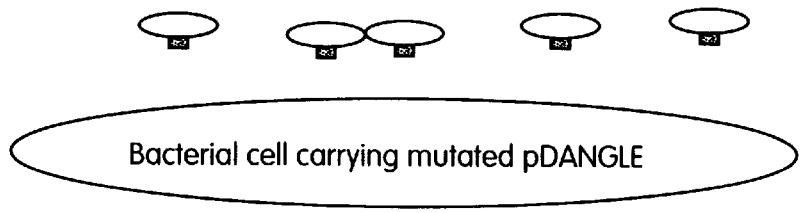
Figure 6D:
Figure 6E:
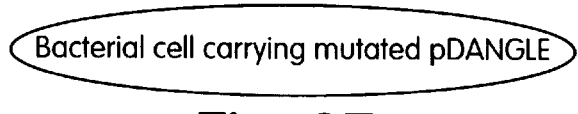

Screening and Selection Procedures a) Screening: The library is plated so as to obtain individual colonies. Each individual colony is then screened for production of soluble protease outlined as follows. Following mutagenesis and transformation into competent BL21 cells, transformants were plated onto Luria-broth agar plates containing ampicillin and incubated at 37° C. overnight. Individual colonies were selected for their resistance to ampicillin and screened for production and secretion of IgA protease as exemplified by binding of anti-IgA protease antibody by immobilised supernatant from the induced growing cultures. Individual colonies were cultured in rich LB media with ampicillin overnight at 37° C. Fresh media was added to the overnight cultures and cell growth at 37° C. monitored. The individual cultures were induced with 0.5 mM IPTG once suspensions had reached log phase. The cultures were returned to 37° C. for 2 hours. Thereafter, the cultures were pelleted by centrifugation at 3000 rpm for 20 minutes at room temperature, and the supernatant harvested. Aliquots of 50 μl of the supernatants were placed into individual wells of a series of flat-bottomed high-binding, 96-well polyvinylchloride EIA/RIA microtitre plates. To each well 50 μl of coating buffer (sodium bicarbonate-sodium carbonate buffer pH 9.6) was added and mixed, the plates were covered, and the supernatant allowed to fix to the plates overnight at 37° C. with gentle shaking. The coated plates were washed four times with wash buffer (0.5 M NaCl, 15 mM $KH_2PO_4$, 65 mM $Na_2HPO_4$) containing 0.05% (v/v) Tween 20. To each well, 100 μl diluted monoclonal antibody was added and the plates incubated for 2 hours at 37° C.; the anti-IgA protease monoclonal antibody purified from supernatant from AH207 hybridoma cultures (hybridoma AH207 was the kind gift of Giovanna Morelli, Max-Planck Institut fuer Molekulare Genetik, Berlin, Germany) was diluted 1:500 in wash buffer containing 0.05% (v/v) Tween 20 and 0.5% (v/v) BSA (to block non-specific binding). After further washing as described, 100 μl of conjugate (rabbit anti-mouse Ig-peroxidase conjugate (Dako) diluted 1:500 in wash buffer+Tween 20+BSA) was added to each well and the incubation repeated as above. After repeated washing as before, 200 μl of freshly-prepared buffered peroxidase substrate (Sigma) solution was added to each well. After 30 minutes at room temperature, the reaction was terminated by the addition of 50 μl of 4 M $H_2SO_4$. Absorbances were read at 490 nm using a Dynex microplate reader (Dynex).

b) Positive Selection: This makes use of a construct as exemplified in FIG. 5C. Such a construct is obtained by substituting the natural cleavage site (AP1 and AP2, FIG. 5) with a cassette or DNA fragment encoding the desired new target sequence upstream of a region encoding an affinity tag. The affinity tag is a protein sequence (e.g., myc tag) able to bind to an immoblised ligand such as a cognate antibody (reference for myc/9E10: Fowlkes, D. M., Adams, M. D., Fowler, V. A., Kay, B. K. (1992) Multipurpose Vectors For Peptide Expression On The M13 Viral Surface Biotechniques 13(3):422) or a small molecule ligand such as nickel bound to a chelating insoluble matrix (in this case the tag is made up of repeating histidine residues). The construct is produced so that the protease domain, target, tag and exporter are all fused to maintain reading frame, thus producing a fusion protein that will translocate the protease domain to the outer surface of the bacterium. The affinity tag will be sterically masked (non-functional) by the large globular protease domain (FIG. 6A). However, upon mutagenesis of the protease-encoding domain (as above) the resultant mutant library will contain four types of constructs. Cells expressing a protease able to cleave a site on the amino terminus side of the tag sequence will secrete soluble protease into the media and leave unmasked (functional) affinity tag (FIG. 6B). In contrast, mutants cleaving downstream of (or within) the affinity tag will produce cells lacking the tag (FIG. 6C). Most mutations will not alter protease specificity and so most cells we be functionally wild type (FIG. 6D) and some will fail to express any protein on the surface (FIG. 6E). Only cells of type shown in FIG. 6B will be able to stick to immobilised ligand. This forms the basis of a positive selection protocol in which pools of each library are subjected to affinity chromatography or biopanning. Cells retained by the affinity matrix (e.g., ligand covalently attached to agarose or magnetic particles) would then be washed with sterile media, allowed to grow and reapplied to the fresh affinity media in an iterative manner. Thus, enrichment for cells carrying engineered protease directed against the desired target region would be obtained.

Precedent for binding of cells carrying exposed 6 His tags was shown for *E. coli* expressing the 6His tag on a surface exposed loop of the LamB protein were able to to bind in a specific manner to nickel chelate agarose beads. Cells could be eluted with immidazole and remained viable. (Sousa, C., Cebolla, A., deLorenzo, V. (1996) Enhanced Metalloadsorption of Bacterial Cells Displaying Poly-His Peptides. *Nature Biotech.* 14(8):1017–1020).

Equivalents

Those skilled in the art will recognize, or be able to ascertain using no more than routine experimentation, many equivalents to the specific embodiments of the invention described herein. Such equivalents are intended to be encompassed by the following claims.

REFERENCES

Cregg, J. M. et al. (1993) Recent Advances in the Expression of Foreign Genes in *Pichia pastoris. Bio/Technology* 11:905–910.

Eglinton, et al. "Site-directed mutagenesis to study protein structure and function" in *Laboratory Methods in Immunology*, editor, Zola, H., CRC Press, Inc., Boca Raton, Fla., Vol. 1, Chapter 16, p. 195–206.

Furlan, M. et al. (1997) Deficient activity of von Willebrand factor-cleaving protease in chronic relapsing thrombotic thrombocytopenic purpura. *Blood* 89(9):3097–3103.

Gilbert, et al. (1988) Cloning of the gene encoding streptococcal immunoglobulin A protease and its expression in *Escherichia coli. Infect. Immun.* 56(8):1961–1966.

Gilboa, E. et al. (1986) Transfer and expression of cloned genes using retroviral vectors. *BioTechniques* 4(6):504–512.

Kadowaki, T. et al. (1994) *J. Biol. Chem.* 629:21371–21378.

Klauser, et al. (1993) The secretion pathway of IgA protease-type proteins in gram-negative bacteria. *Bioessays* 15(12):799–805.

Koomey, et al. (1982) Genetic and biochemical analysis of gonococcal IgA1 protease: cloning in *Escherichia coli* and construction of mutants of gonococci that fail to produce the activity. *Proc. Natl. Acad. Sci. (USA)* 79(24):7881–7885.

Meyer, et al. (1987) Mechanism of extracellular secretion of an IgA protease by gram-negative host cells. *Adv. Exp. Med. Biol.* 216B:1271–1281.

Mildner, et al. (1994) The HIV-1 protease as enzyme and substrate: mutagenesis of autolysis sites and generation of a stable mutant with retained kinetic properties. *Biochem.* 33:9405–9413.

Miller, et al. (1992) Endoglucanase A from *Cellulomonas fimi* in which the hinge sequence of human IgA1 is substituted for the linker connecting its two domains is hydrolyzed by IgA proteases from *Neisseria gonorrhoeae. FEMS Microbiol. Lett.* 71(2):199–203.

Morton, et al. (1993) Purification and characterization of chimeric human IgA1 and IgA2 expressed in COS and Chinese hamster ovary cells. *J. Immunol.* 151(9):4743–4752.

Pohlner, et al. (1987) *Neisseria gonorrhoeae* IgA protease. Secretion and implications for pathogenesis. *Antonie Van Leeuwenhoek* 53(6):479–484.

Pohlner, et al. (1992) Sequence-specific cleavage of protein fusions using a recombinant Neisseria type 2 IgA protease. *Biotechnology (NY)* 10(7):799–804.

Pohlner, et al. (1993) A plasmid system for high-level expression and in vitro processing of recombinant proteins. *Gene* 130(1):121–126.

Pompejus, et al. (1993) High-yield production of bacteriorhodopsin via expression of a synthetic gene in *Escherichia coli. Eur. J. Biochem.* 211:(1–2):27–35.

Sayer, et al. (1992) Rapid high efficiency site-directed mutagenesis by the phosphorthioate approach. *BioTechniques* 13:592–596.

Stemmer, (1994) Rapid evolution of a protein in vitro by DNA shuffling. *Nature* 370:389–39.

Tomasselli, et al. (1990) Substrate analogue inhibition and active site titration of purified recombinant HIV-1 protease. *Biochem.* 29:264–269.

Vitorski, S. et al. (1999) *FASEB J.* 13:331–337.

Walker, et al. (1994) Efficient and rapid affinity purification of proteins using recombinant fusion proteases. *Biotechnology (NY)*, 12(6):601–605.

Wong and Nathoo (1994) Engineering and production of streptokinase in a *Bacillus subtilis* expression-secretion system. *Appl. Environ. Microbiol.* 60(2):517–523.

Zoller and Smith (1982) Oligonucleotide-directed mutagenesis using M13-derived vectors: an efficient and general procedure for the production of point mutations in any fragment of DNA. *Nucl. Acids Res.* 10(20):6487–6500.

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial  Sequence: Primer

<400> SEQUENCE: 1
acccttaaaa cggtaaaacc ttatg                                              25

<210> SEQ ID NO 2
<211> LENGTH: 30
<212> TYPE: DNA
<213> ORGANISM: Artificial Sequence
<220> FEATURE:
<223> OTHER INFORMATION: Description of Artificial  Sequence: Primer

<400> SEQUENCE: 2
agaggatccg gagcggtctt gtacggatga                                         30

<210> SEQ ID NO 3
<211> LENGTH: 22
<212> TYPE: DNA
<213> ORGANISM: Artificial Sequence
<220> FEATURE:
<223> OTHER INFORMATION: Description of Artificial  Sequence: Primer

<400> SEQUENCE: 3
tcaggaaggg ctgaatctct tt                                                 22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial  Sequence: Primer

<400> SEQUENCE: 4
atgccgtcta gagcctgagt tc                                                 22

<210> SEQ ID NO 5
<211> LENGTH: 38
<212> TYPE: PRT
<213> ORGANISM: Unknown Organism
<220> FEATURE:
<223> OTHER INFORMATION: Description of Unknown Organism: Bacterial
      Iga Protease

<400> SEQUENCE: 5

Pro Val Pro Ser Pro Ala Thr Asn Thr Ala S er Gln Ala Gln Thr Asp
 1               5                  10                  15

Ser Ala Gln Ile Ala Lys Pro Gln Asn Ile V al Val Ala Pro Pro Ser
            20                  25                  30

Pro Gln Ala Asn Gln Ala
        35

<210> SEQ ID NO 6
<211> LENGTH: 38
<212> TYPE: PRT
<213> ORGANISM: Unknown Organism
<220> FEATURE:
<223> OTHER INFORMATION: Description of Unknown Organism: Bacterial

```
                        Iga Protease

<400> SEQUENCE: 6

Pro Val Glu Ser Pro Ala Thr Asn Thr Ala S er Gln Ala Gln Thr Asp
  1               5                  10                  15

Ser Ala Gln Ile Ala Lys Pro Gln Asn Ile V al Val Ala Pro Glu Ser
             20                  25                  30

Pro Gln Ala Asn Gln Ala
         35

<210> SEQ ID NO 7
<211> LENGTH: 12
<212> TYPE: PRT
<213> ORGANISM: Unknown Organism
<220> FEATURE:
<223> OTHER INFORMATION: Description of Unknown Organism: Bacterial
      Iga Protease

<400> SEQUENCE: 7

Pro His His His His His His Gln Ala Asn G ln Ala
  1               5                  10
```

What is claimed is:

1. A method for obtaining a target specific protease, comprising the steps of:
   a) providing a DNA vector encoding a modified self-secreting endoprotease, wherein said endoprotease is comprised of a signal peptide sequence, an endoprotease catalytic domain, a target cleavage site of a target protein and a carboxy-terminal domain;
   b) obtaining a library of said vectors, wherein the DNA encoding the endoprotease catalytic domain has been mutagenized; and
   c) isolating from said library a vector that expresses a target specific protease that is able to cleave the target cleavage site of said target protein.

2. The method of claim 1, wherein the endoprotease catalytic domain is an IgA endoprotease catalytic domain.

3. The method of claim 1, wherein said target cleavage site is identical to a sequence present in a target protein selected from the group consisting of: a cytokine, a cytokine receptor, a clotting factor, a gene product of an oncogene, a gene product of an anti-oncogene, a mutant protein that causes a genetic disorder, a viral protein, a bacterial protein, and a polypeptide-containing toxin or environmental or industrial pollutant.

4. The method of claim 1, wherein said target protein is overexpressed in humans having a disease.

5. The method of claim 1 or 4, wherein said target protein is selected from the group consisting of HIV-1 protease, HIV-1 reverse transcriptase, HIV-1 integrase, HIV-1 gp120, HIV-1 gp41, urokinase-type plasminogen activator, tissue-type plasminogen activator, neutrophil elastase, argingipain, von Willebrand factor, p53 and Her-2/neu.

6. The method of claim 1, wherein the library of vectors in step (b) is obtained by site directed mutagenesis or Stemmer gene shuffling.

7. The method of claim 1 or 4, wherein the library obtained in step (b) is transferred to a bacterial host cell which can express the protease products.

8. The method of claim 1 or 4, further comprising step (d) wherein steps (b) and (c) are repeated until the desired endoprotease catalytic domain specificity is obtained.

9. The method of claim 1, wherein the isolation of said vector from said library comprises a negative selection wherein a cell expressing IgA protease on its surface is depleted.

10. The method of claim 1, wherein the isolation of said vector from said library comprises a positive selection.

11. The method of claim 1, wherein the isolation of said vector from said library comprises detection of the endoprotease catalytic domain which is liberated upon cleavage of said target cleavage site.

12. The method of claim 1, further including the step of isolating cells producing a protein comprising the mutagenized endoprotease catalytic domain which cleaves said target cleavage site of said target protein.

13. The method of claim 1, wherein said modified self-secreting enoprotease further comprises an affinity tag which can be used in a positive selection procedure to select bacteria containing a vector encoding a protease catalytic domain which cleaves the target cleavage site and unmasks the affinity tag.

14. The method of claim 13, wherein the affinity tag is able to bind to an immobilized ligand.

15. A modified self-secreting endoprotease which has been engineered to cleave a user-defined target cleavage site, said endoprotease comprising:
   (a) a signal peptide sequence,
   (b) an endoprotease catalytic domain,
   (c) a target cleavage site and
   (d) a carboxy-terminal domain.

16. The modified self-secreting endoprotease of claim 15, further comprising an affinity tag.

17. The modified self-secreting endoprotease of claim 15, wherein said protease catalytic domain is a mutant protease catalytic domain which cleaves said target cleavage site.

* * * * *